United States Patent [19]

Wesley

[11] 4,004,718
[45] Jan. 25, 1977

[54] SYRINGES

[75] Inventor: Frank Wesley, Sidcup, England

[73] Assignee: Societe d'Assistance Technique pour Produits Nestle S.A., Lausanne, Switzerland

[22] Filed: May 23, 1974

[21] Appl. No.: 472,838

Related U.S. Application Data

[63] Continuation of Ser. No. 182,075, Sept. 20, 1971.

[52] U.S. Cl. .......................... 222/386; 128/218 C
[51] Int. Cl.² ........................................ B67D 1/08
[58] Field of Search .......... 285/DIG. 12, 353, 354; 222/309, 386, 49; 128/218 C, 218 R, 218 N, 218

[56] References Cited
UNITED STATES PATENTS

| | | | |
|---|---|---|---|
| 2,855,927 | 10/1958 | Henderson | 128/218 |
| 3,101,084 | 8/1963 | Hamilton | 128/218 |
| 3,393,930 | 7/1968 | Ziherl et al. | 285/334.4 |
| 3,521,795 | 7/1970 | Langhjelm et al. | 222/386 |
| 3,606,086 | 9/1971 | Drummond et al. | 222/49 |

*Primary Examiner*—Allen N. Knowles
*Assistant Examiner*—Norman L. Stack, Jr.
*Attorney, Agent, or Firm*—Watson Leavenworth Kelton & Taggart

[57] ABSTRACT

A syringe, especially for measuring microliter amounts, which comprises a barrel having over at least a part of its length an inner liner composed of a resilient plastics material surrounding a bore and a piston slidable within the liner bore, the maximum cross-sectional area of the piston being slightly greater than the cross-sectional area of the undeformed bore. The liner is preferably made of a polytetrafluoroethylene and the piston comprises a wire with a bead at one end. A method of attaching a needle to the syringe is also disclosed.

7 Claims, 2 Drawing Figures

SYRINGES

This is a continuation of application Ser. No. 182,075, filed Sept. 20, 1971.

This invention relates to syringes for dispensing small volumes of fluids.

Syringes generally comprise a parallel-sided barrel with a piston inside, the barrel normally being of glass, and a needle mounted at the end of the barrel through which the fluid to be dispensed is drawn and ejected by sliding the piston within the barrel. Such syringes are normally satisfactory for handling clear fluids of low viscosity but are less satisfactory when liquids of high viscosity such as certain concentrated solutions are handled. Because of capillary resistance to flow, these liquids take an appreciable time to pass through the needle and as a fully gas-tight seal cannot be maintained between the piston and the barrel, several "pumping" steps are generally necessary to fill the syringe.

This fault is especially troublesome in "microsyringes", i.e. syringes of small bore which contain volumes of the order of one micro-litre, because there is appreciable resistance to flow through the narrow barrel as well as through the needle. Such microsyringes are used in many scientific fields, for example thin layer and gas chromatography, where a small, accurately known volume of liquid is required to be delivered from the needle.

An object of the present invention is to provide a syringe which has an improved seal between the piston and the barrel so that the time required for filling is considerably reduced.

The syringe according to the invention comprises a barrel having an inner liner composed of a resilient plastics material surrounding a bore and a slidable piston within the liner, the maximum cross-sectional area of the piston being slightly greater than the cross-sectional area of the undeformed bore.

As the piston has a greater cross-sectional area than the bore, the portion of the resilient liner surrounding the piston is deformed and a relatively tight, substantially impervious seal is obtained between the piston and the liner. A relatively high vacuum is therefore obtained in the syringe when the piston is withdrawn, so that liquids of relatively high viscosity can be handled without pumping. The maximum cross-sectional area of the piston is preferably not more than 0.05 mm$^2$ greater than that of the undeformed liner.

The piston and the bore are preferably of circular cross-section and the liner is desirably composed of a low-friction material such as polytetrafluoroethylene, so that little force is required to displace the piston.

A needle may be attached to the end of the barrel by means of a screw fitting and a substantially gas-tight seal between the needle and the barrel is provided by a flexible annular plug, preferably of an inert material such as soft polyvinyl chloride or silicone rubber, which is compressed within the screw fitting. The portion of the screw fitting which is mounted on the barrel is preferably held in place by a flange portion of the fitting which abuts an annular protrusion around the end of the barrel. A cushioning washer of a flexible material such as asbestos is preferably placed between the flange and the protrusion to relieve local excess pressure on the protrusion.

A preferred embodiment of the invention will be described, by way of illustration only, with reference to the accompanying drawings, in which.

Figure 1:
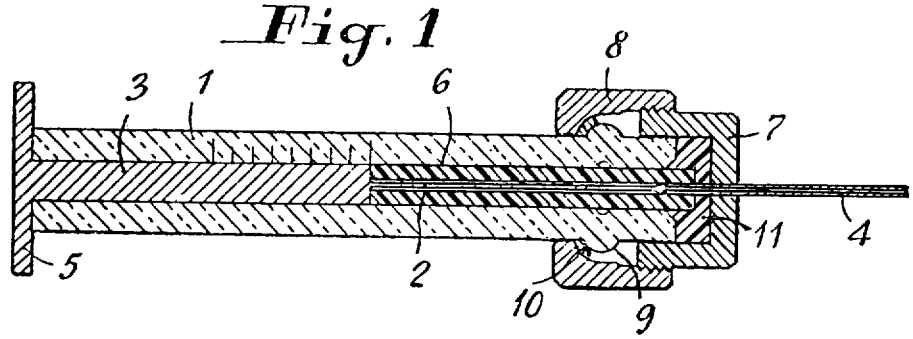
FIG. 1 is a longitudinal section of a syringe according to the invention.
Figure 2:
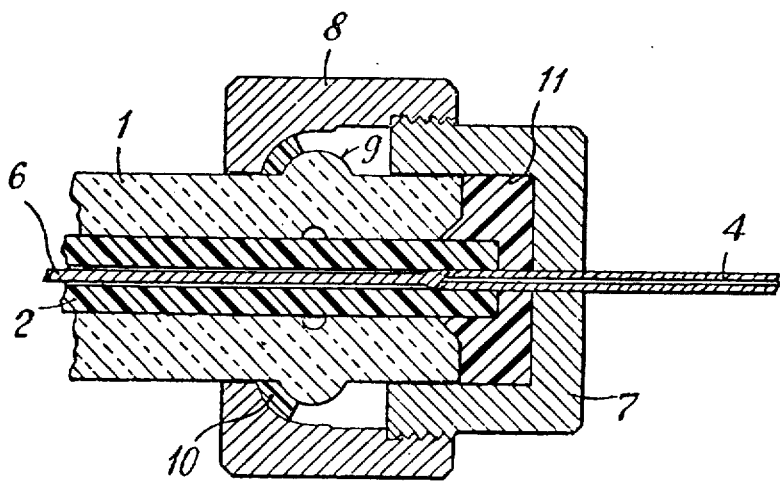
FIG. 2 is a portion of FIG. 1 on an enlarged scale.

As shown in the drawing, the syringe has a glass barrel 1 the lower portion of which has a liner 2 of a low-friction resilient plastics material such as polytetrafluoroethylene. One end of the liner protrudes a short distance beyond the end of the barrel. The barrel and liner are each of substantially constant internal cross-section and a metal plunger 3 slides freely in the upper part of the barrel which has graduations etched on its surface. Plunger 3 may be slid along the barrel by pressing or withdrawing thumb button 5 and it is rigidly attached to a stiff wire 6 which slides freely within the liner 2. Wire 6 has a metal bead at its end, a diameter slightly greater than the internal diameter of the undeformed liner 2 and hence forms a substantially gas-tight seal. However, because of the slight flexibility of the liner in the barrel and the low friction properties of the material of which the liner is composed, the piston bead can slide relatively freely within the liner when the plunger is depressed or withdrawn.

The protruding end of the liner 2 surrounds one end of the needle 4 through which fluid is drawn into the syringe so that the fluid is drawn directly into the lined portion of the barrel. Liner 2 and needle 4 are retained in position by an annular plug 11, preferably of soft polyvinyl chloride or silicone rubber, or other flexible resilient material which fits tightly around the protruding portion of the liner and the part of the needle adjacent the barrel. Plug 11 is held in position by externally threaded cap 7, preferably of stainless steel, which is screwed into the internally threaded collar 8, also preferably of stainless steel, which surrounds the barrel. Collar 8 has a flange portion which engages an annular protrusion 9 on the barrel, thereby holding the collar in position when it engages the cap 7. A cushioning washer 10 of a soft material such as asbestos, is placed between the protrusion and the flange portion to prevent localised excess pressure on the protrusion.

The construction according to the invention is especially useful when applied to syringes having a bore of very narrow calibre, such as micro-syringes having a cross-sectional area not exceeding 0.3 mm$^2$, because with a narrow bore the flow resistance of liquids is especially great. Furthermore, the syringe has the advantage that it is free from permanently cemented joints, so that the various components, especially the needle, may readily be replaced. A further advantage is that the syringe may be sterilised at a high temperature, e.g. by autoclaving. This is not possible with conventional cemented-joint syringes, as such heating tends to destroy the cements which are normally used for sealing the needle into the barrel. The assembly does not require precisely-mated joints and so all the components are relatively cheap. The inner end of the needle is preferably inserted in and surrounded by the end of the liner in order to minimise the "dead volume" between the needle and the barrel when the piston is fully depressed.

I claim:

1. A syringe which comprises an elongated transparent barrel, an elongated plunger disposed in said barrel and slidable along a first length thereof, an inner liner in said barrel disposed along the remaining length of said barrel, said liner being comprised of a resilient plastics material and extending in an encircling course enclosing a space defining a bore of normally substantially constant cross-sectional dimension, said bore providing a reservoir for holding a fluid, and a piston connected to said plunger extending coaxially therewith and within the liner bore for sliding travel in said bore when said plunger is slid in said barrel first section, said first length of said barrel being graduated to indicate the volume of fluid in the syringe, the cross-sectional area of at least a tip end portion of said piston being greater than the cross-sectional area of said liner bore, said liner bore enlargingly deforming when said piston tip end slides in said liner to maintain a substantially gas tight seal between said piston tip end portion and said liner.

2. A syringe according to claim 1 in which the piston comprises a wire having a bead at one end thereof, the end of the wire remote from said bead being connected to said plunger.

3. A syringe according to claim 1 in which the plastics material is a polytetrafluoroethylene.

4. A syringe according to claim 1 in which the maximum cross-sectional area of the piston is not more than 0.05 mm$^2$ greater than the cross-sectional area of the undeformed liner.

5. A syringe according to claim 4 in which the cross-sectional area of the bore is not greater than 0.3 mm$^2$.

6. In combination with a syringe according to claim 1, a needle coaxial with the barrel with the inner end of the needle inserted within the liner and adjacent to but spaced from the tip end portion of said piston when said plunger is slid to its maximum travel position in the direction of said needle, the end of the liner protruding from the barrel and being surrounded by a plug of resilient material which is retained under compression.

7. The combination of claim 6 in which the plug is retained under compression by a threaded cap which engages a threaded collar mounted on the end of the barrel, the collar being retained on the end of the barrel by engagement with an annular protrusion around the barrel and a cushioning washer of flexible material is positioned between the protrusion and the collar.

* * * * *